United States Patent [19]

Towe

[11] Patent Number: 4,583,545
[45] Date of Patent: Apr. 22, 1986

[54] NONINVASIVE BIOMAGNESONIC METHOD OF BIOCURRENT MEASUREMENT

[76] Inventor: Bruce C. Towe, 2331 S. Paseo Loma Cir., Mesa, Ariz. 85202

[21] Appl. No.: 627,597

[22] Filed: Jul. 3, 1984

[51] Int. Cl.$^4$ ............................................. A61B 5/00
[52] U.S. Cl. .................................................... 128/630
[58] Field of Search ............ 128/773, 653, 630, 1.3–1.5

[56] References Cited

U.S. PATENT DOCUMENTS 4,134,395  1/1979  Davis ................................. 128/1.3
4,385,634  5/1983  Bowen ............................... 128/653

FOREIGN PATENT DOCUMENTS 8103226  5/1980  World Int. Prop. O. .......... 128/653

Primary Examiner—Kyle L. Howell
Assistant Examiner—David Shay
Attorney, Agent, or Firm—Cahill, Sutton & Thomas

[57] ABSTRACT

An arrangement for noninvasively detecting both alternating and direct biocurrents in a living organism applies a magnetic field to the organism, such that a biocurrent flowing in the organism interacts with the applied magnetic field to generate a force in the tissue of the organism at the location of the biocurrent, producing an acoustic response thereat. The acoustic response is detected by placing at least one acoustic transducer detector, such as a microphone, in proximity to the organism, such that the detected acoustic response corresponds to the biocurrent. The applied magnetic field can be generated by a circular array of magnetic field generators placed symmetrically about the organism. The applied magnetic field can be rotated relative to the organism by selectively energizing opposite pairs of magnetic field generators in sequence. An array of acoustic detectors can be placed in proximity to the organism, such that the timed response of each detector in relationship to the timed response of the other detectors or to the phase of the applied magnetic field provides information on the magnitude and location of the biocurrent.

23 Claims, 5 Drawing Figures

NONINVASIVE BIOMAGNESONIC METHOD OF BIOCURRENT MEASUREMENT

BACKGROUND OF THE INVENTION

1. Field of the Invention

The present invention relates generally to an arrangement for noninvasively detecting biocurrents in an organism, and more particularly pertains to a method of noninvasively detecting both alternating and direct biocurrents in living organisms which is implemented in an extremely useful medical diagnostic instrument.

2. Discussion of the Prior Art

The flow of electric currents in a biological organism play a major role in its life processes. Small biocurrents range in magnitude from one microampere, associated with the firing of a small nerve, to almost one milliampere, occurring during a heart muscle contraction. Biocurrents are generally known to be associated with the heart, muscle and nervous systems. In addition, biocurrents are known to be generated during the growth process and also during the process of wound healing in tissue. Within the past several years it has also become generally recognized that injured, diseased, or cancerous tissues also generate bioelectric currents. These currents, unlike pulsing muscle and nerve currents, are steady in magnitude and appear immediately with the injury or tumor and disappear only if the problem disappears. It is known, for example, that the heart generates an "injury current" coincident with a heart attack which is apparently proportional in magnitude to the amount of tissue affected. It is also known that the degree of malignancy of a cancer tumor is related to the magnitude of its generated bioelectric current, and also that benign cysts, for example, generate no biocurrents.

The measurement of DC biocurrents has been extremely difficult in particular. Very low frequency and direct currents are difficult to impossible to measure noninvasively at present, yet are known to carry significant diagnostic and prognostic information relating to both heart disease and cancer. Skin electrodes do not work well at all as noise and artifacts generated by biopotential electrodes obscure any small potentials appearing on the skin from diseased internal organs. The study of DC currents has been conducted by researchers by surgically placing electrodes directly on the tissue of interest, which has not resulted in satisfactory measurements.

SUMMARY OF THE INVENTION

Accordingly, it is a primary object of the present invention to provide an arrangement for noninvasively detecting biocurrents in living organisms.

A further object of the subject invention is the provision of an arrangement as described for noninvasively detecting both alternating and direct biocurrents which has utility in providing diagnostic and prognostic information relating to heart disease, cancer and other areas of medical interest. A particularly attractive application of the present invention is for the detection of breast cancer in women which has the specific advantage of being able to differentiate malignant from benign tumors, which is something other noninvasive diagnostic techniques have not been able to accomplish.

In accordance with the teachings herein, the present invention provides a unique method of detecting biocurrents in a living organism for assisting in a medical diagnosis thereon. A magnetic field is applied to the organism, such that a biocurrent flowing in the organism interacts with the applied magnetic field to generate a force in the tissue of the organism at the location of the biocurrent, which produces an acoustic response in the tissue. The acoustic response is detected by placing at least one acoustic transducer detector, such as a microphone, in proximity to the organism, such that the detected acoustic response corresponds to the biocurrent.

In greater detail, in one preferred embodiment of the present invention, the magnetic field is generated by a circular array of magnetic field generators placed symmetrically about the organism. In this embodiment, the applied magnetic field can be rotated relative to the organism by selectively energizing opposite pairs of magnetic field generators in sequence, such that the magnetic field extends between each of an opposite pair of magnetic field generators, and is rotated as another opposite pair of magnetic field generators is energized.

In one preferred mode of operation, a periodic magnetic field is applied to the organism, and the acoustic response is synchronously detected, which enables very low frequency and direct biocurrents to be detected. In a further refinement, first and second periodic magnetic fields are applied at first and second different frequencies, with the generated magnetic fields at the first and second frequencies having different spatial gradient characteristics. For instance, the first magnetic field can be chosen to have a high spatial gradient characteristic, while the second magnetic field gradient is chosen to have a low or constant spatial gradient characteristic. The acoustic response is measured separately at the first and second frequencies, which provides positional information on the detected biocurrent. Essentially, two separate equations with two unknowns should enable the calculation of the biocurrent location and biocurrent magnitude which would satisfy the equations.

Moreover, in a preferred embodiment of the present invention, a circular array of acoustic detectors is placed in proximity to the organism, such that the timed response of each detector in relationship to the timed response of the other detectors or in a timed relationship to the phase of the applied magnetic field in the array provides information on the location and magnitude of the biocurrent. The feature of the circular array of acoustic detectors can be advantageously combined with the feature of a circular array of magnetic field generators to provide relatively complete information on the position and magnitude of the detected biocurrent, utilizing currently known data processing techniques such as correlations of the data including auto correlation and cross correlation, and Fourier transforms thereof.

In preferred embodiments, each acoustic transducer detector is shielded from the applied magnetic field to prevent magnetic feedback thereto. Alternatively, an acoustic pick-up probe or monitor can be placed on the surface of the organism, such that the acoustic response is transmitted to a remote electrical acoustic transducer to prevent magnetic feedback thereto from the magnetic field.

BRIEF DESCRIPTION OF THE DRAWINGS

The foregoing objects and advantages of the present invention for a noninvasive biomagnesonic method of biocurrent measurement may be more readily understood by one skilled in the art with reference being had to the following detailed description of several preferred embodiments thereof, taken in conjunction with the accompanying drawings in which.

DETAILED DESCRIPTION OF THE INVENTION

Figure 1:
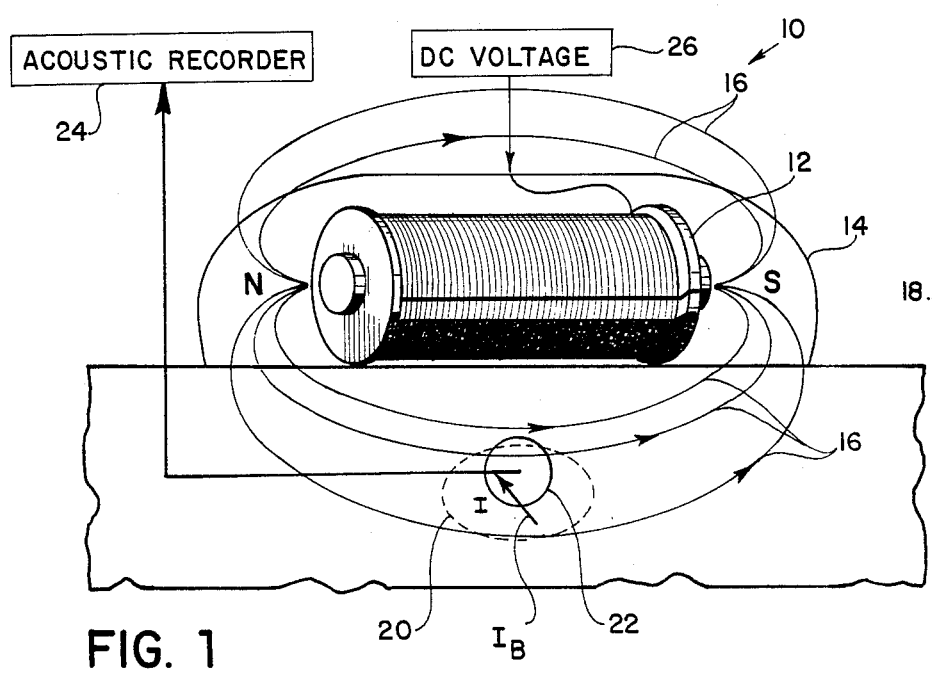
FIG. 1 is a first schematic exemplary embodiment of a somewhat basic biomagnesonic diagnostic arrangement constructed pursuant to the teachings of the present invention.

Maxwell's equations describing the interaction of electric and magnetic fields indicate that a current carrying conductor in a magnetic field will experience a force given by:

$$F = \int_v (J \times B)\, dv$$

where F is the force in Newtons, B is the magnetic field flux density, and J is the current density. Research has also confirmed that the equation applies equally well to the flow of charged ions constituting a current flow in fluids. Ion currents flow in biological objects, and such currents are responsible for muscle contraction, nerve impulse conduction, and for homeostatic mechanisms. Current flow in body tissue placed in a strong magnetic field will likewise generate a force in the tissue in a direction orthonormal to the applied magnetic field and the current vector. Since body tissue is an elastic medium, this force will cause a momentary displacement of the tissue, and thus create a corresponding small pressure or acoustic wave of amplitude and duration proportional to the time course of the current flow. The applied magnetic field can be a direct or steady state field such as is available from a permanent magnet. Alternatively, the applied magnetic field can be alternated at a frequency which is high compared to the time duration and frequency of the bioelectric events being detected which then generates an acoustic wave at a frequency equal to that of the applied magnetic field and with an amplitude proportional to the bioelectric current time course and magnitude. A sensitive contact microphone is placed on the skin or surface of the living organism, and the acoustic wave is synchronously detected, such that applied low level simulated biocurrents flowing through the organism can be detected from the generated acoustic waves. Furthermore, the resultant acoustic waves readily propagate through the biological medium following well understood laws, and can be detected a distance away from the current source by the microphone.

It has been found to be fairly important in the practice of the present invention to prevent either physical, electrical, or magnetic feedback between the magnetic field generator and the microphone acoustical detector(s). Two techniques can be employed to minimize this feedback, physically removing the microphone(s) from the magnetic generator by an acoustic transport arrangement similar in concept to a stethoscope, and shielding of the microphone(s) with a shield similar to a Faraday shield.

In general, the present invention has the following characteristics:

1. Acoustic waves travel at a finite speed in a given medium (about 1500 m/sec. in tissue). The distance the acoustical source is away from the detector can be determined by applying a magnetic pulse to a biocurrent source and then noting the delay time before the acoustic wave reaches the microphone. This gives the depth of the biocurrent source. Multiple biocurrent acoustic sources overlying one another in a line to the microphone can be separated and measured independently by noting the time delays between the individual acoustic waves. Although somewhat different in operating principles, medical diagnostic ultrasonic imaging uses echo transit time delays of applied ultrasonic sound waves in a similar manner to generate depth information.

2. The emission of the evoked acoustic wave from the biocurrent source is somewhat directional since it results from the cross product of the current vector and magnetic field vectors. Accordingly, in principle, three dimensional direction of the current flow can be determined through the correlation of an array of multiple acoustic detectors. Moreover, in accordance with one embodiment of the present invention, the magnetic field is generated by a spaced array, such as a circular array, of magnetic field generators. This advantageously allows the magnetic field to be rotated relative to the organism while a plurality of readings are taken by either one or an array of microphones. The combination of an array of magnetic generators, for sequentially rotating the magnetic field, and an array of microphones for detecting the acoustical response at different locations, yields a tremendous amount of diagnostic information which can be correlated for a rather precise definition of both the magnitude and direction of the biocurrent vector. Three dimensional imaging of the biocurrents is possible using the techniques described herein, which can provide a medical diagnostic imaging system of the same nature as ultrasound and NMR scanning diagnostic systems.

3. Very low frequency and direct currents can be measured through the use of alternating applied magnetic fields. These currents are difficult to impossible to measure noninvasively at present, yet carry significant diagnostic information on heart disease and cancer.

4. Spatial X-Y resolution is obtained by directing and scanning the magnetic fields.

5. The low frequency evoked acoustical waves travel through tissue with relatively little attenuation, and thus the detector need not be in direct contact with the source, but can be some distance away to allow noninvasive detection.

Referring to the drawings in detail, FIG. 1 illustrates a first schematic and exemplary embodiment 10 of a somewhat basic biomagnesonic diagnostic arrangement constructed pursuant to the teachings of the present invention and comprising a magnetic field generator 12 shown mounted in a movable housing 14. The resultant magnetic field lines 16 extend freely into a body portion 18 and through a tissue area of interest 20. In this particular example, the tissue area 20 being examined has a biocurrent associated therewith represented by the current vector $I_B$. An acoustical transducer detector 22, such as a microphone, examines the area of interest for acoustical signals. The output of the acoustical detector can be recorded as a function of time at 24, or could be displayed.

The magnetic field generator 12 is illustrated as a magnetic core surrounded by an electrical coil, such that when a voltage is initially applied thereto from a DC voltage source 26, a magnetic field is applied to the organism, such that the biocurrent flowing in the organism interacts with the applied magnetic field 16 to generate a force in the tissue of the organism at the location of the biocurrent, which produces an acoustic response in the tissue. The acoustic response is then detected by the acoustic transducer detector or microphone and recorded or displayed.

Figure 2:
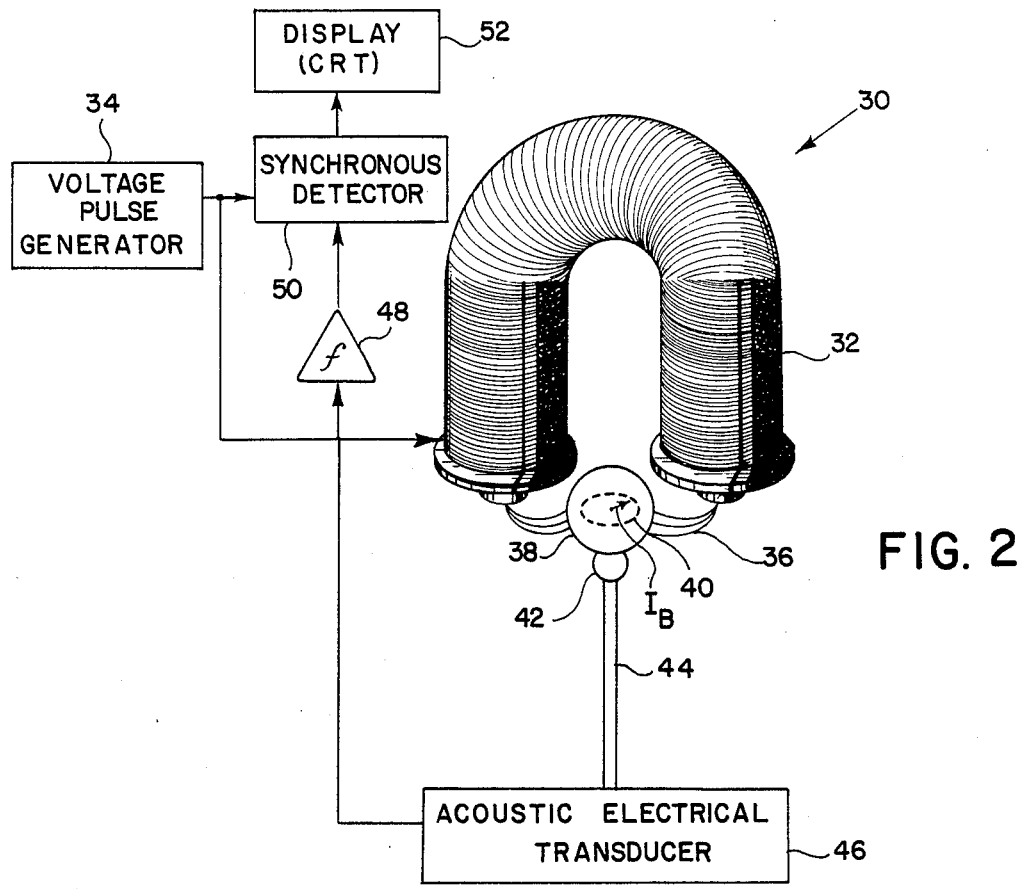
FIG. 2 illustrates a somewhat schematic arrangement of a second embodiment of the subject invention.

FIG. 2 illustrates a somewhat schematic arrangement of a second embodiment 30 of the subject invention wherein a U shaped electromagnetic field generator 32 is periodically actuated by a voltage pulse from a generator 34 to generate a magnetic field 36, between oppositely positioned poles of the magnetic field generator 32. An organism 38 is placed in the magnetic field 36, and in this exemplary illustration, the organism 38 has a particular tissue area of interest 40 having a biocurrent $I_B$ associated therewith. Alternatively, the poles of the magnetic field generator can be directly facing each other, such that the organism is placed in the gap between the oppositely positioned magnetic poles. In this embodiment, an acoustic pick-up probe 42, similar in concept to those utilized in a stethoscope, is placed on the surface of the organism, such that the acoustic response is transmitted through a carrier tube 44 to a remote electrical acoustic transducer 46. The remote placement of the electrical transducer 46 effectively prevents electrical, magnetic or physical coupling thereto of the applied magnetic field as it has been found to be fairly important in the practice of the present invention to prevent either physical, electrical, or magnetic feedback between the magnetic field generator and the microphone acoustical detector(s).

In operation, voltage pulses are periodically applied to the magnetic field generator to produce a periodic magnetic field in the organism 38. Because of the presence of $I_B$, a periodic electrical output signal is produced by detector 46, and is directed through a filter 48, which passes only the bandwidth of interest, to a synchronous detector 50, which also receives synchronizing pulses from generator 34. The output of the synchronous detector 50 is then displayed, as on a CRT display 52, and could also be recorded. This arrangement should be particularly of interest in the detection of low frequency and direct biocurrents.

Figure 3:
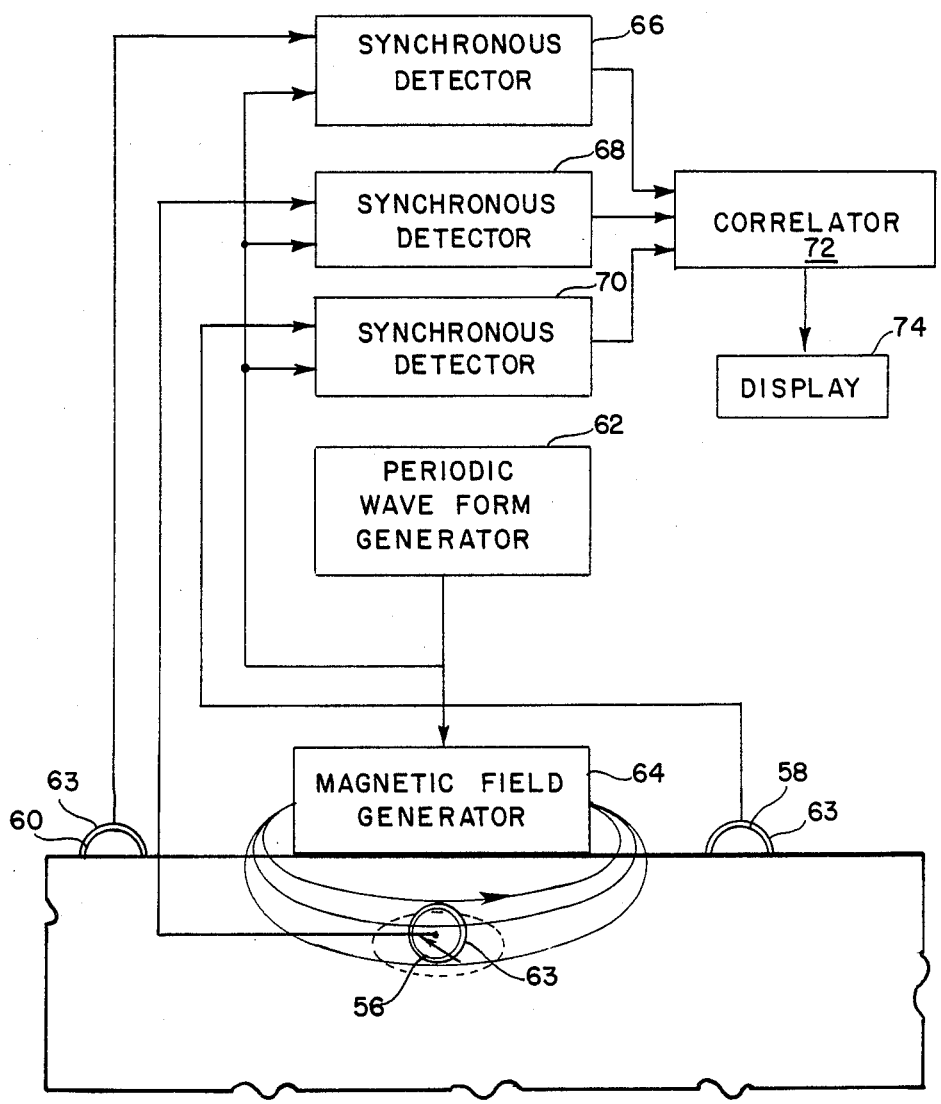
FIG. 3 illustrates a more refined embodiment of the present invention wherein an array of acoustic transducers provides positional information on the detected biocurrent.

FIG. 3 illustrates a more refined embodiment of the present invention wherein a circular array of acoustic transducers 56, 58 and 60 provides positional and magnitude information on the detected biocurrent $I_B$. A periodic waveform generator 62, which could for example be a pulse train generator or a sine wave generator or any other suitable periodic waveform generator, generates a periodic waveform which is directed to a magnetic field generator 64. The periodic waveform is also applied to three synchronous detectors 66, 68 and 70, which are also coupled respectively to the three acoustic-electrical transducers. Each of the three synchronous detectors provides a detected response, timed with respect to the periodic waveform. Accordingly, the detected response of each detector can be compared or correlated at 72 with the timed responses of the other detectors in the array to provide analytical information on the position and magnitude of the detected biocurrent which is then displayed at 74 and/or recorded. In this embodiment, each acoustic-electrical transducer 56, 58 and 60, which can be a suitable commercially available microphone, is shielded by a conductive shield 63 similar in concept to a Faraday shield to minimize magnetic and electrical coupling thereto from the applied magnetic field.

A refinement of the present invention which could be practiced with the embodiment of FIG. 3 involves generating magnetic fields at different frequencies, with different characteristics, and then comparing the detected responses. For example, first and second periodic magnetic fields can be generated at first and second different frequencies, for example by using a voltage controlled oscillator as periodic waveform generator 62 operated at two different frequencies by two input voltage levels, with the generated magnetic fields at the first and second frequencies having different magnetic gradient characteristics. For instance, the first magnetic field can be chosen to have a high spatial gradient characteristic, while the second magnetic field is chosen to have a low or constant spatial gradient characteristic. The acoustic response is measured separately at the first and second frequencies, which provides positional information on the detected biocurrent. Essentially, two separate equations with two unknowns should enable the calculation of the biocurrent location and biocurrent magnitude which would satisfy the equations.

Figure 4:
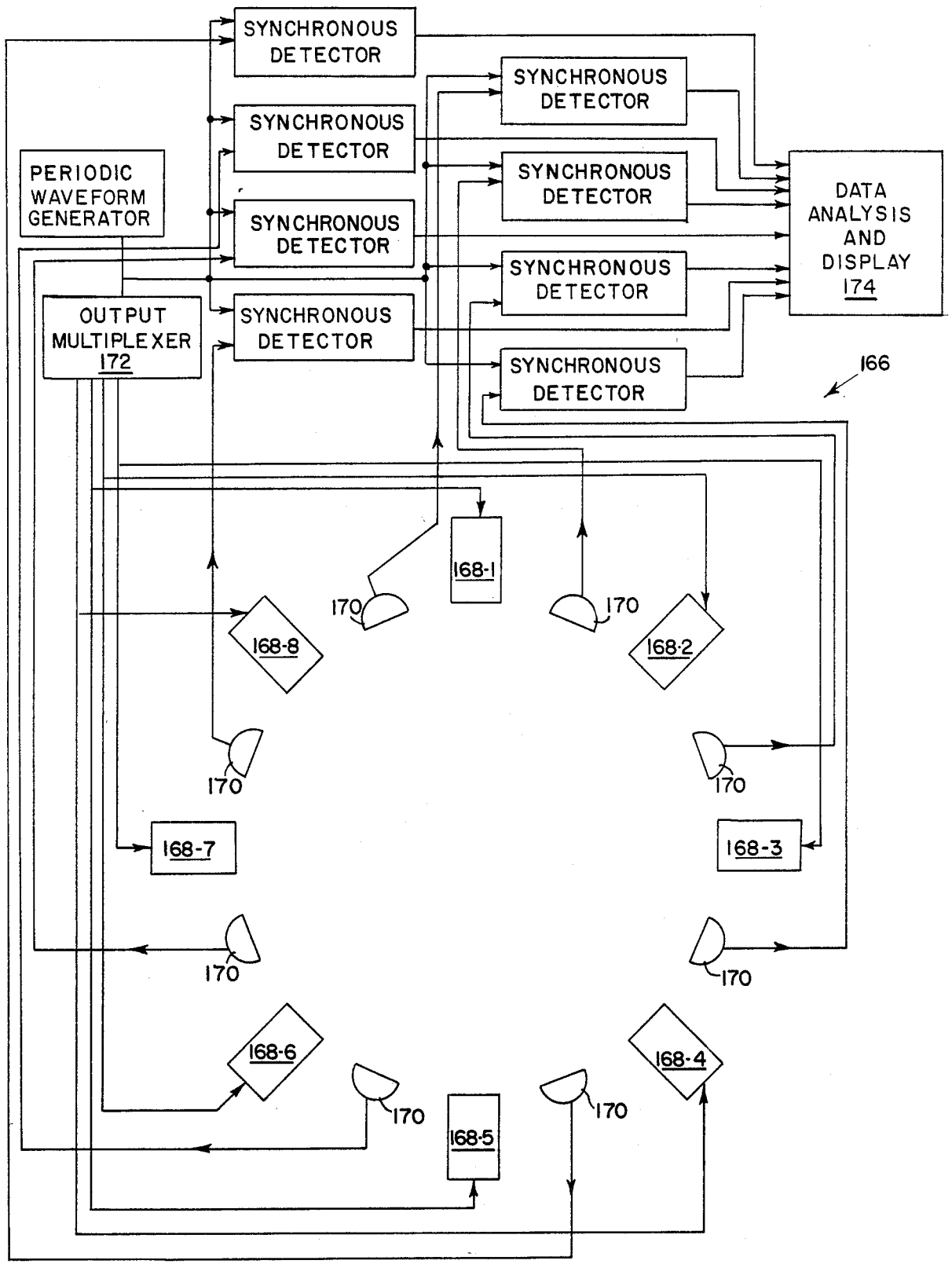
FIG. 4 illustrates a preferred embodiment of a biomagnesonic diagnostic instrument constructed pursuant to the principles of the present invention, with the instrument employing circular arrays of both magnetic generators and acoustic transducers.

FIG. 4 illustrates a preferred embodiment of a biomagnesonic diagnostic instrument 166 constructed pursuant to the principles of the present invention, with the instrument employing a circular array of eight magnetic generators 168-1 through 168-8 and a circular array of eight acoustic transducers 170. In this embodiment, the organism being diagnosed, such as a chest or breast, is placed within the inner cavity of the instrument within the circular arrays. One or more of the transducers 170 is then placed against the surface of the organism. This embodiment advantageously provides for the magnetic field to be applied in any one of four directions, or reversed for eight directions. Moreover, in this embodiment, the applied magnetic field can be rotated relative to the organism by an output multiplexer 172 which energizes opposite pairs of magnetic field generators in sequence, such that the magnetic field extends between each of an opposite pair of magnetic field generators such as 168-1 and 168-5, and is rotated as another opposite pair of magnetic field generators, such as 168-2 and 168-6, is energized.

The outputs of one or more of the detectors 170 is synchronously detected and the data in the various magnetic scans is then analyzed at 174 utilizing currently known data processing techniques such as correlations of the data including auto correlation and cross correlation and Fourier transforms thereof. The final diagnostic output is then displayed and/or recorded as appropriate.

Figure 5:
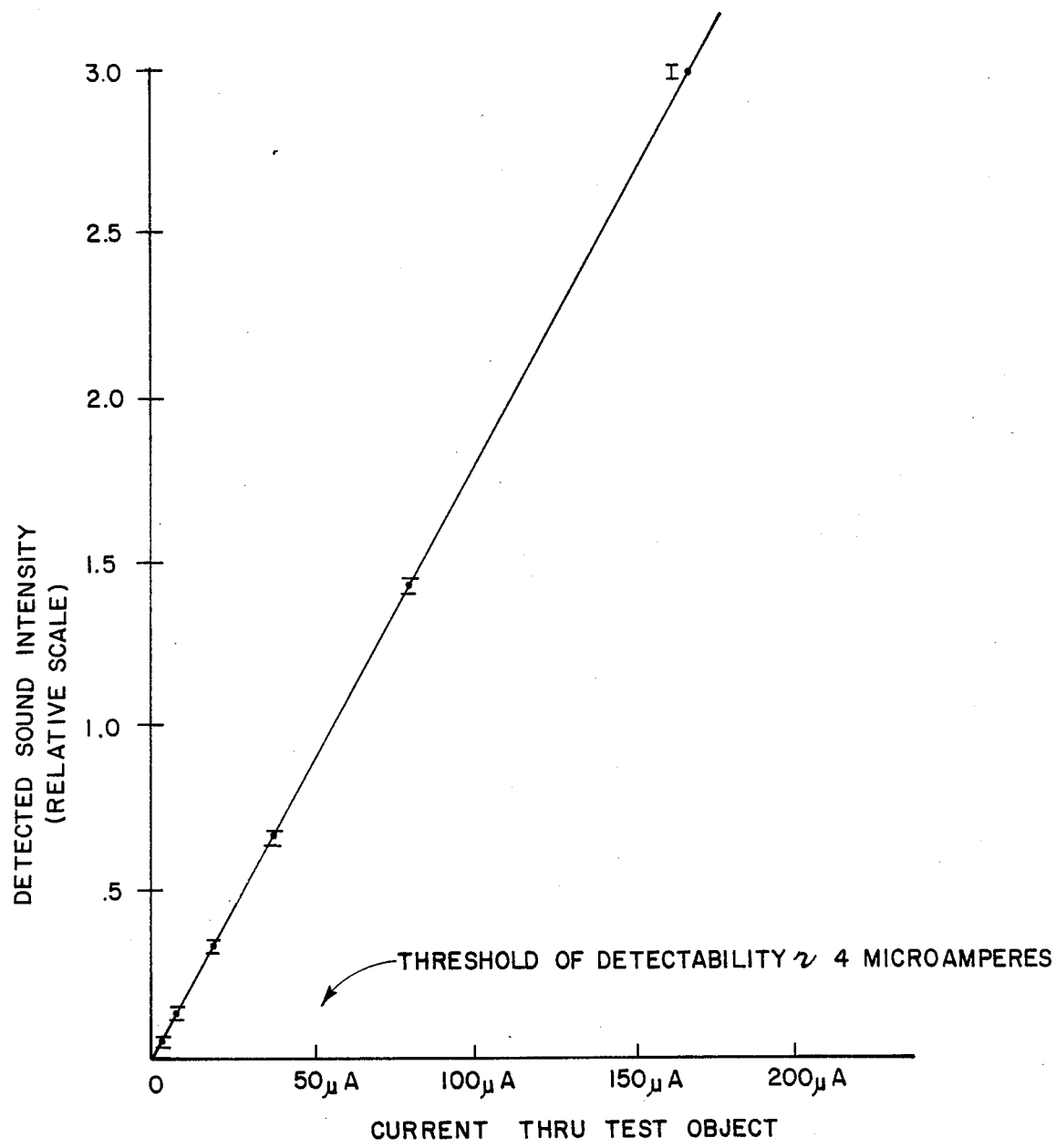
FIG. 5 is a graph of the amplitude of magnetosonically generated acoustic waves as a function of applied current for a 5000 Gauss permanent magnet field generator.

FIG. 5 is a graph of the amplitude of magnetosonically generated acoustic waves as a function of applied current for a 5000 Gauss permanent magnetic field generator. This data was obtained on a simulated biological source in which a low level current was passed through conductive saline filled silastic tubing. The tubing was placed in a magnet field generated by a permanent magnetic in one case, and an AC electromagnet in another. A sensitive microphone was placed several inches away and contacted the silastic tubing by means of a saline filled glass tube sound conductor. Acoustic waves were generated in the silastic tubing positioned in the bore of the magnet when various currents were applied. The vibration propagated to the microphone through the acoustic link which simulated attenuation equivalent to the intervening tissue loss. In general, to be useful in medical diagnoses, biocurrents in the range of below 100 microamperes must be detected. FIG. 5 illustrates that currents in this range can be detected by this technique. However, relatively strong magnetic fields (about 5000 Gauss) are necessary for this operation.

While several embodiments and variations of the present invention for a noninvasive method of detecting biocurrents are described in detail herein, it should be apparent that the disclosure and teachings of the present invention will suggest many alternative designs to those skilled in the art. For instance, in the described embodiments, a periodic magnetic field is applied relative to the organism by varying the magnetic field. However, it is also possible to apply a periodic magnetic field relative to the organism by rotating the organism within a steady state magnetic field.

What is claimed is:

1. A noninvasive method of detecting biocurrents in an organism, comprising the steps of:
   a. applying a magnetic field to the organism; such that a biocurrent flowing in the organism interacts with the applied magnetic field to generate a force in the tissue of the organism at the location of the biocurrent in a direction orthogonal to the applied magnetic field and the biocurrent, thereby producing an acoustic response in the tissue;
   b. detecting any acoustic response by placing at least one acoustic transducer detector in proximity to the organism, whereby the detected acoustic response corresponds to the biocurrent.

2. A noninvasive method of detecting biocurrents in an organism according to claim 1, wherein said step of detecting the acoustic response comprises shielding the at least one acoustic transducer detector from the applied magnetic field to prevent magnetic feedback thereto.

3. A noninvasive method of detecting biocurrents in an organism according to claim 1, wherein said step of detecting the acoustic response comprises placing an acoustic pick-up probe on the surface of the organism, and transmitting the acoustic response to a remote electrical acoustic transducer to prevent magnetic feedback from the applied magnetic field to the remote electrical acoustic transducer.

4. A noninvasive method of detecting biocurrents in an organism according to claim 1, wherein said step of detecting the acoustic response comprises the step of detecting the acoustic response by placing an array of acoustic detectors in proximity to the organism, whereby the timed response of each detector in relationship to the timed response of the other detectors in the array and the applied magnetic field provides positional information on the location of the biocurrent in the organism.

5. A noninvasive method of detecting biocurrents in an organism according to claim 4, wherein said array of acoustic detectors comprises a circular array of detectors which is placed symetrically about the organism.

6. A noninvasive method of detecting biocurrents in an organism according to claim 1, wherein said step of applying a magnetic field to the organism includes the step of positioning a plurality of magnetic field generators in a circular array symmetrically about the organism and periodically actuating said plurality of magnetic field generators.

7. A noninvasive method of detecting biocurrents in an organism according to claim 6, wherein said step of applying a magnetic field further comprises the step of rotating the applied magnetic field relative to the organism.

8. A noninvasive method of detecting biocurrents in an organism according to claim 7, wherein said step of rotating the applied magnetic field comprises the step of selectively energizing opposite pairs of magnetic field generators in sequence, such that the magnetic field extends between each of an opposite pair of magnetic field generators, and is rotated as another opposite pair of magentic field generators is energized.

9. A noninvasive method of detecting biocurrents in an organism according to claim 1, wherein said step of applying a magnetic field comprises generating a magnetic field between oppositely positioned magnetic poles placed on opposite sides of the organism.

10. A noninvasive method of detecting biocurrents in an organism according to claim 1, wherein said step of applying a magnetic field comprises the step of applying a periodic magnetic field relative to the organism, whereby very low frequency and direct biocurrents can be detected.

11. A noninvasive method of detecting biocurrents in an organism for a medical diagnosis thereon according to claim 10, wherein said step of applying a periodic magnetic field comprises applying first and second periodic magnetic fields at first and second frequencies having first and second different spatial gradient characteristics to provide additional diagnostic information on the detected biocurrent, which allows the calculation of both the biocurrent magnitude and position in the organism through the correlation of the detected acoustic responses and the known magnetic field gradients.

12. A noninvasive method of detecting biocurrents in an organism, comprising the steps of:
   a. generating a period magnetic field of a predetermined frequency;
   b. applying said periodic magnetic field to the organism such that a biocurrent flowing in the organism interacts with the applied magnetic field to generate a force in the tissue of the organism at the location of the biocurrent in a direction orthogonal to the applied magnetic field and the biocurrent, thereby producing an acoustic response in the tissue;
   c. placing at least one acoustic transducer detector in proximity to the organism for detecting acoustical signals and producing an electrical output signal in response thereto; and
   d. filtering from said electrical output signal a detected signal corresponding to said predetermined frequency for detecting any acoustic responses corresponding to the biocurrent flowing in the organism.

13. The noninvasive method of detecting biocurrents in an organism as recited by claim 12 wherein said step of generating a periodic magnetic field includes the step of periodically actuating an electromagnetic field generator. to create said periodic magnetic field.

14. A noninvastive method of detecting biocurrents in an organism as recited by claim 13 wherein said step of periodically actuating the electromagnetic field generator includes the step of providing periodic waveform signals of said predetermined frequency and coupling the periodic waveform signals to said electromagnetic field generator.

15. A noninvasive method of detecting biocurrents in an organism as recited by claim 14 wherein said filtering step includes the steps of:
   a. providing pulses synchronized with the periodic waveform signals to a synchronous detector; and
   b. coupling the electrical output signal produced by said acoustic transducer detector to said synchronous detector for providing the detected signal.

16. A noninvasive method of detecting biocurrents in an organism as recited by claim 12 wherein said step of placing at least one acoustic transducer detector includes the step of shielding said acoustic transducer detector from the applied periodic magnetic field to prevent magnetic feedback thereto.

17. A noninvasive method of detecting biocurrents in an organism as recited by claim 12 wherein said step of placing at least one acoustic transducer detector includes the step of placing an acoustic pick-up probe on the surface of the organism and transmitting the acoustic response to a remote electrical acoustic transducer to prevent magnetic feedback from the applied magnetic field to the remote electrical acoustic transducer.

18. A noninvasive method of detecting biocurrents in an organism as recited by claim 12 wherein said step of placing at least one acoustic transducer detector includes the step of placing an array of acoustic detectors in proximity to the organism for providing positional information on the location of the biocurrent in the organism based upon the timed response of each acoustic detector within said array of acoustic detectors in relationship to the timed response of the other detectors in said array.

19. A noninvasive method of detecting biocurrents in an organism as recited by claim 18 wherein said step of placing said array of acoustic detectors includes the step of placing said array of acoustic detectors in a circle symmetrically about the organism.

20. A noninvasive method of detecting biocurrents in an organism as recited by claim 12 wherein said step of applying said periodic magnetic field to said organism includes the step of positioning a plurality of electromagnetic field generators in a circular array symmetrically about the organism and periodically actuating said plurality of electromagnetic field generators.

21. A noninvasive method of detecting biocurrents in an organism as recited by claim 20 wherein said step of applying a magnetic field further includes the step of rotating the applied magnetic field relative to the organism.

22. A noninvasive method of detecting biocurrents in an organism as recited by claim 21 wherein said step of rotating the applied magnetic field includes the step of selectively energizing opposite pairs of said magnetic field generators in sequence to provide a magnetic field which extends between each of an opposite pair of energized magnetic field generators, and wherein said periodic magnetic field is rotated as another opposite pair of magnetic field generators is energized.

23. A noninvasive method of detecting biocurrents in an organism as recited by claim 12 wherein said steps of generating and applying said periodic magnetic field include the steps of generating and applying first and second periodic magnetic fields of first and second frequencies, respectively, and having first and second different spatial gradient characteristics, and wherein said filtering step includes the steps of filtering from said electrical output signal a detected signal corresponding to one of said first and second frequencies for detecting any acoustic responses corresponding to the biocurrent.

* * * * *